US008778009B2

(12) United States Patent
Kreidler et al.

(10) Patent No.: US 8,778,009 B2
(45) Date of Patent: Jul. 15, 2014

(54) INTRAVASCULAR STENT

(75) Inventors: Marc S. Kreidler, Sunnyvale, CA (US);
Jessica P. Miller, Santa Clara, CA (US)

(73) Assignee: Abbott Cardiovascular Systems Inc.,
Santa Clara, CA (US)

( * ) Notice: Subject to any disclaimer, the term of this patent is extended or adjusted under 35 U.S.C. 154(b) by 1134 days.

(21) Appl. No.: 11/544,256

(22) Filed: Oct. 6, 2006

(65) Prior Publication Data
US 2008/0086194 A1    Apr. 10, 2008

(51) Int. Cl.
*A61F 2/06*    (2013.01)

(52) U.S. Cl.
USPC ......................................................... 623/1.15

(58) Field of Classification Search
CPC ............. A61F 2/915; A61F 2/89; A61F 2/82; A61F 2/86; A61F 2002/9155; A61F 2002/91558
USPC ........................ 623/1.11, 1.15, 1.13, 1.18, 1.2
See application file for complete search history.

(56) References Cited

U.S. PATENT DOCUMENTS

| 4,580,568 | A | 4/1986 | Gianturco |
| 5,102,417 | A | 4/1992 | Palmaz |
| 5,104,404 | A | 4/1992 | Wolff |
| 5,292,331 | A | 3/1994 | Boneau |
| 5,449,373 | A | 9/1995 | Pinchasik et al. |
| 5,607,442 | A | 3/1997 | Fischell et al. |
| 5,632,771 | A | 5/1997 | Boatman et al. |
| 5,643,312 | A | 7/1997 | Fischell et al. |
| 5,669,932 | A | 9/1997 | Fischell et al. |
| 5,674,241 | A | 10/1997 | Bley et al. |
| 5,674,278 | A | 10/1997 | Boneau |
| 5,697,971 | A | 12/1997 | Fischell et al. |
| 5,733,303 | A | 3/1998 | Israel et al. |
| 5,741,327 | A | 4/1998 | Frantzen |
| 5,755,781 | A | 5/1998 | Jayaraman |
| 5,776,161 | A | 7/1998 | Globerman |
| 5,807,404 | A | 9/1998 | Richter |
| 5,810,872 | A | 9/1998 | Kanesaka et al. |
| 5,824,040 | A | 10/1998 | Cox et al. |
| 5,827,321 | A | 10/1998 | Roubin et al. |

(Continued)

FOREIGN PATENT DOCUMENTS

DE    29708 879 U1    9/1997
EP    0 372 789 A3    6/1990

(Continued)

OTHER PUBLICATIONS

U.S. patent application Publication No. 2001/0044649 A1 to Vallana et al. published Nov. 22, 2001.
U.S. patent application Publication No. 2001/0044652 A1 to Moore published Nov. 22, 2001.
U.S. patent application Publication No. 2001/0044653 A1 to Kveen et al. published Nov. 22, 2001.

(Continued)

*Primary Examiner* — Thomas McEvoy
*Assistant Examiner* — Julie A Szpira
(74) *Attorney, Agent, or Firm* — Fulwider Patton LLP

(57) ABSTRACT

A stent design reduces the likelihood of contact among structural members when the stent diameter is reduced before insertion into the body. In one approach, an undulating link has a J-shaped profile or has an angled portion on one side at the peak of the link, in order to reduce contact during crimping. The stent may also include structural features that improve such aspects as flexibility, the coatibility of a drug coating onto the stent, flare reduction, stent retention within the body and/or reduction of the minimum diameter of the stent during crimping.

42 Claims, 10 Drawing Sheets

(56) References Cited

U.S. PATENT DOCUMENTS

| | | |
|---|---|---|
| 5,836,964 A | 11/1998 | Richter et al. |
| 5,843,120 A | 12/1998 | Israel et al. |
| 5,843,175 A | 12/1998 | Frantzen |
| 5,853,419 A | 12/1998 | Imran |
| 5,868,781 A | 2/1999 | Killion |
| 5,868,783 A | 2/1999 | Tower |
| 5,876,449 A | 3/1999 | Starck et al. |
| 5,879,370 A | 3/1999 | Fischell et al. |
| 5,879,382 A | 3/1999 | Boneau |
| 5,893,887 A | 4/1999 | Jayaraman |
| 5,911,754 A | 6/1999 | Kanesaka et al. |
| 5,913,895 A | 6/1999 | Burpee et al. |
| 5,922,005 A | 7/1999 | Richter et al. |
| 5,922,020 A | 7/1999 | Klein et al. |
| 5,925,061 A | 7/1999 | Ogi et al. |
| 5,931,866 A | 8/1999 | Frantzen |
| 5,935,162 A | 8/1999 | Dang |
| 5,938,682 A | 8/1999 | Hojeibane et al. |
| 5,938,697 A | 8/1999 | Killion et al. |
| 5,948,016 A | 9/1999 | Jang |
| 5,954,743 A | 9/1999 | Jang |
| 5,964,798 A | 10/1999 | Imran |
| 5,967,986 A | 10/1999 | Cimochowski et al. |
| 5,968,093 A | 10/1999 | Kranz |
| 5,972,018 A | 10/1999 | Israel et al. |
| 5,980,552 A | 11/1999 | Pinchasik et al. |
| 5,993,489 A | 11/1999 | Lewis et al. |
| 6,001,125 A | 12/1999 | Golds et al. |
| 6,004,348 A | 12/1999 | Banas et al. |
| 6,013,091 A | 1/2000 | Ley et al. |
| 6,017,365 A | 1/2000 | Von Oepen |
| 6,019,789 A | 2/2000 | Dinh et al. |
| 6,022,371 A | 2/2000 | Killion |
| 6,022,374 A | 2/2000 | Imran |
| 6,033,433 A | 3/2000 | Ehr et al. |
| 6,033,435 A | 3/2000 | Penn et al. |
| 6,039,755 A | 3/2000 | Edwin et al. |
| 6,039,756 A | 3/2000 | Jang |
| 6,042,597 A | 3/2000 | Kveen et al. |
| 6,042,606 A | 3/2000 | Frantzen |
| 6,048,361 A | 4/2000 | Von Oepen |
| 6,051,020 A | 4/2000 | Goicoechea et al. |
| 6,053,940 A | 4/2000 | Wijay |
| 6,053,941 A | 4/2000 | Lindenberg et al. |
| 6,053,943 A | 4/2000 | Edwin et al. |
| 6,056,775 A | 5/2000 | Borghi et al. |
| 6,056,776 A | 5/2000 | Lau et al. |
| 6,059,822 A | 5/2000 | Kanesaka et al. |
| 6,063,113 A | 5/2000 | Kavteladze et al. |
| 6,066,168 A | 5/2000 | Lau et al. |
| 6,066,169 A | 5/2000 | McGuinness |
| 6,068,656 A | 5/2000 | Von Oepen |
| 6,071,298 A | 6/2000 | Lashinski et al. |
| 6,077,297 A | 6/2000 | Robinson et al. |
| 6,080,191 A | 6/2000 | Summers |
| 6,083,259 A | 7/2000 | Frantzen |
| 6,086,604 A | 7/2000 | Fischell et al. |
| 6,086,611 A | 7/2000 | Duffy et al. |
| 6,090,127 A | 7/2000 | Globerman |
| 6,093,199 A | 7/2000 | Brown et al. |
| 6,093,203 A | 7/2000 | Uflacker |
| 6,099,455 A | 8/2000 | Columbo et al. |
| 6,099,559 A | 8/2000 | Nolting |
| 6,099,560 A | 8/2000 | Penn et al. |
| 6,099,561 A | 8/2000 | Alt |
| 6,102,940 A | 8/2000 | Robichon et al. |
| 6,106,548 A | 8/2000 | Roubin et al. |
| 6,113,627 A | 9/2000 | Jang |
| 6,113,628 A | 9/2000 | Borghi |
| 6,117,165 A | 9/2000 | Becker |
| 6,123,721 A | 9/2000 | Jang |
| 6,129,754 A | 10/2000 | Kanesaka et al. |
| 6,129,755 A | 10/2000 | Mathis et al. |
| 6,149,682 A | 11/2000 | Frid |
| 6,152,957 A | 11/2000 | Jang |
| 6,156,052 A | 12/2000 | Richter et al. |
| 6,162,243 A | 12/2000 | Gray et al. |
| 6,179,868 B1 | 1/2001 | Burpee et al. |
| 6,183,506 B1 | 2/2001 | Penn et al. |
| 6,187,034 B1 | 2/2001 | Frantzen |
| 6,190,403 B1 | 2/2001 | Fischell et al. |
| 6,200,334 B1 | 3/2001 | Jang |
| 6,206,916 B1 | 3/2001 | Furst |
| 6,217,608 B1 | 4/2001 | Penn et al. |
| 6,241,762 B1 | 6/2001 | Shanley |
| 6,258,116 B1 | 7/2001 | Hojeibane |
| 6,264,688 B1 | 7/2001 | Herklotz et al. |
| 6,309,414 B1 | 10/2001 | Rolando et al. |
| 6,325,821 B1 | 12/2001 | Gaschino et al. |
| 6,330,884 B1 | 12/2001 | Kim |
| 6,342,067 B1 | 1/2002 | Mathis et al. |
| 6,348,065 B1 | 2/2002 | Brown et al. |
| 6,375,677 B1 | 4/2002 | Penn et al. |
| 6,451,049 B2 | 9/2002 | Vallana et al. |
| 6,497,723 B1 | 12/2002 | Starck et al. |
| 6,540,775 B1 | 4/2003 | Fischell et al. |
| 6,616,689 B1 * | 9/2003 | Ainsworth et al. ......... 623/1.16 |
| 6,629,994 B2 * | 10/2003 | Gomez et al. ................ 623/1.15 |
| 6,656,220 B1 * | 12/2003 | Gomez et al. ................ 623/1.15 |
| 6,846,323 B2 | 1/2005 | Yip et al. |
| 7,083,642 B2 * | 8/2006 | Sirhan et al. ................. 623/1.42 |
| 2002/0111672 A1 | 8/2002 | Kim et al. |
| 2002/0123797 A1 | 9/2002 | Majercak |
| 2003/0040790 A1 | 2/2003 | Furst |
| 2004/0088040 A1 * | 5/2004 | Mangiardi et al. .......... 623/1.15 |
| 2006/0052860 A1 * | 3/2006 | Gomez et al. ................ 623/1.15 |

FOREIGN PATENT DOCUMENTS

| | | |
|---|---|---|
| EP | 0 088 093 B1 | 1/1999 |
| EP | 0 888 757 A1 | 1/1999 |
| EP | 1 088 528 A1 | 4/2001 |
| EP | 1236445 | 4/2002 |
| EP | 2374431 A2 | 10/2011 |
| JP | 11-104246 | 4/1999 |
| JP | 2005253558 A | 9/2005 |
| WO | WO 95/03010 | 2/1995 |
| WO | WO 98/22159 | 5/1998 |
| WO | 9915108 | 1/1999 |
| WO | WO 99/02105 | 1/1999 |
| WO | WO 99/17680 | 4/1999 |
| WO | WO 00/30563 | 6/2000 |
| WO | WO 00/42945 | 7/2000 |
| WO | WO 00/42946 | 7/2000 |
| WO | WO 00/62710 | 10/2000 |
| WO | WO 02/24111 A2 | 3/2002 |
| WO | 03061527 A1 | 7/2003 |
| WO | 2004047613 A2 | 6/2004 |
| WO | 2006035669 A1 | 4/2006 |

OTHER PUBLICATIONS

U.S. patent application Publication No. 2002/0007212 A1 to Brown et al. published Jan. 17, 2002.

U.S. patent application Publication No. 2002/0023843 A1 to Cherkes published Feb. 28, 2002.

U.S. patent application Publication No. 2002/0032478 A1 to Boekstegers et al. published Mar. 14, 2002.

U.S. patent application Publication No. 2002/0045933 A1 to Jang published Apr. 18, 2002.

U.S. patent application Publication No. 2002/0045934 A1 to Jang published Apr. 18, 2002.

U.S. patent application Publication No. 2002/0045935 A1 to Jang published Apr. 18, 2002.

U.S. patent application Publication No. 2002/0058989 A1 to Chen et al. published May 16, 2002.

U.S. patent application Publication No. 2002/0058990 A1 to Jang published May 16, 2002.

U.S. patent application Publication No. 2002/0073792 A1 to Burgermeister et al. published Jun. 13, 2002.

* cited by examiner

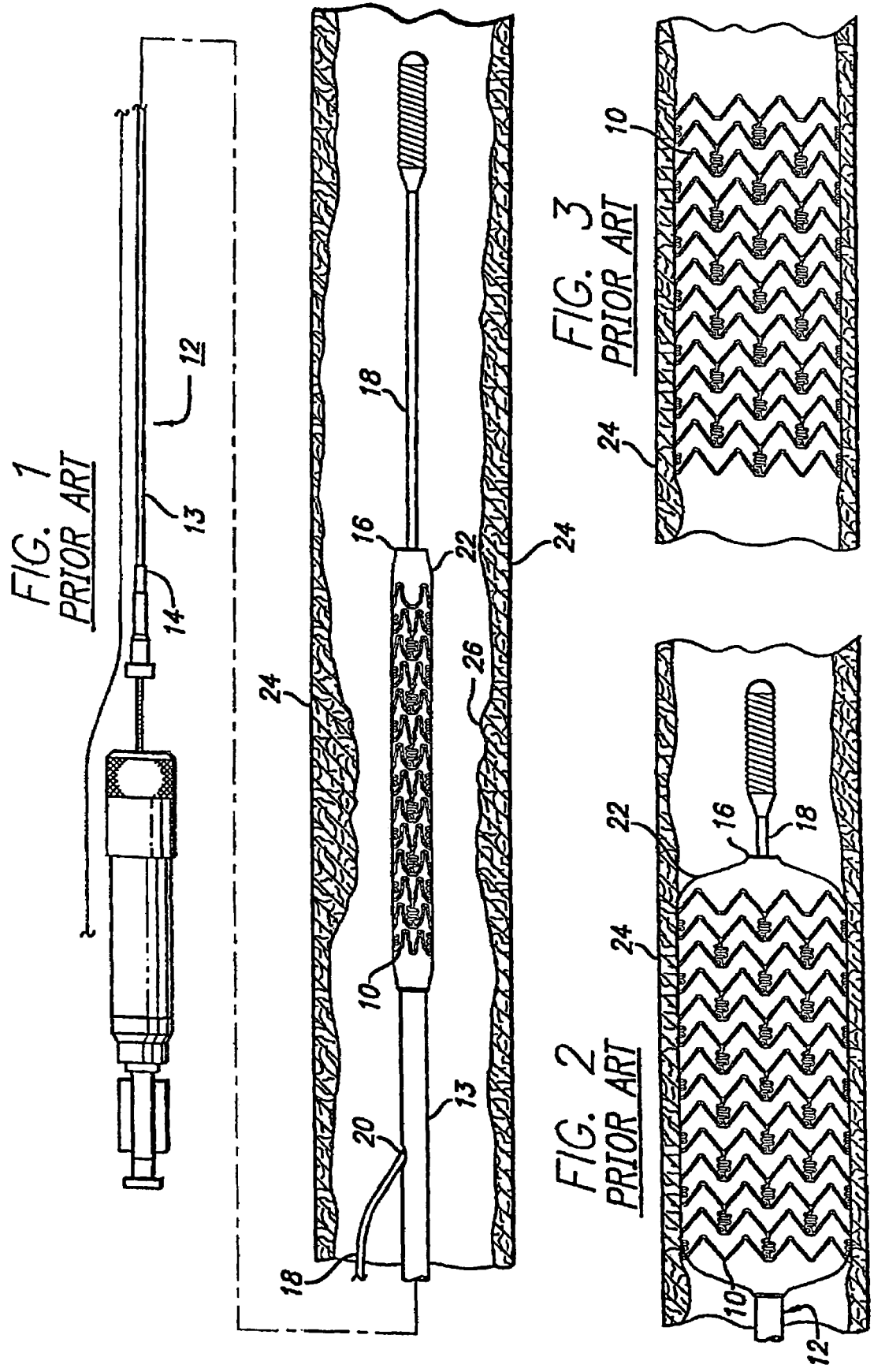

INTRAVASCULAR STENT

BACKGROUND OF THE INVENTION

The invention relates to vascular repair devices, and in particular intravascular stents, which are adapted to be implanted into a patient's body lumen, such as a blood vessel or coronary artery.

Stents are generally tubular-shaped devices that hold open a segment of a blood vessel or other body lumen such as a coronary artery. They also are suitable to support and hold back a dissected arterial lining that can occlude the fluid passageway. There are many known stents, such as those disclosed in U.S. Pat. No. 6,629,994, entitled "Intravascular Stent" and issued on Oct. 7, 2003, which is incorporated by reference herein.

The prior art stents depicted in FIGS. 1-5 have multiplex cylindrical rings connected by one or more undulating links. While some of these stents are flexible and have the appropriate radial rigidity needed to hold open a vessel or artery, there typically is a tradeoff between flexibility, radial strength, and the ability to tightly compress or crimp the stent onto a catheter. Crimping the stent is important so that it does not move relative to the catheter or dislodge prematurely prior to controlled implantation in a vessel.

In these prior art stents, each of the cylindrical rings making up the stent has proximal and distal ends, and a cylindrical plane defined by a cylindrical outer wall surface that extends circumferentially between the proximal end and the distal end of the cylindrical ring. Generally, the cylindrical rings have a serpentine or undulating shape that includes one or more U-shaped elements. The cylindrical rings are interconnected by at least one undulating link that attaches one cylindrical ring to an adjacent cylindrical ring.

The undulating links may take various configurations but, in general, have an undulating or serpentine shape. The undulating links can include bends connected by substantially straight portions wherein the substantially straight portions are substantially perpendicular to the stent longitudinal axis.

The cylindrical rings typically are formed of a plurality of peaks and valleys, where the valleys of one cylindrical ring are circumferentially offset from the valleys of an adjacent cylindrical ring. In this configuration, at least one undulating link attaches each cylindrical ring to an adjacent cylindrical ring so that at least a portion of the undulating links is positioned within one of the valleys and it attaches the valley to an adjacent peak.

While the cylindrical rings and undulating links generally are not separate structures, they have been conveniently referred to as rings and links for ease of identification. Further, the cylindrical rings can often be thought of as comprising a series of U's, W's and other-shaped structures in a repeating pattern. Again, while the cylindrical rings are not divided up or segmented into U's, W's and other shapes, the pattern of the cylindrical rings resemble such configuration. The U's, W's and other shapes promote flexibility in the stent primarily by flexing and by tipping radially outwardly as the stent is delivered through a tortuous vessel.

Although there are many advantages to stents of this type, recent advances in stent design in which the stent is coated with drugs, raise new design challenges. It is important that as the stent is crimped prior to insertion into the body, there is no contact between portions of the stent. This type of contact, as illustrated in FIGS. 6 and 7, can have adverse effects on the drug coating which can, for example, form a bubble and peel off.

What is needed is a flexible and strong stent having very little or no contact between structural members as the stent is crimped prior to insertion into the body. It is also desirable to increase the coatability of the stent, to reduce flaring, and/or to improve stent retention.

SUMMARY OF THE INVENTION

The present invention includes stent designs that reduce the likelihood of contact among structural members when the stent diameter is reduced prior to insertion into the body. In one embodiment, a flexible intravascular stent for use in a body lumen has cylindrical rings aligned along a common longitudinal axis. The rings are interconnected to form the stent. Each cylindrical ring has a first delivery diameter for insertion into the body, and an expanded second diameter after being implanted into the body.

At least some of the cylindrical rings have first peaks and second peaks. In one embodiment, the second peaks are shorter than the first peaks. At least one undulating link attaches each cylindrical ring to an adjacent cylindrical ring. The undulating links have a curved portion that extends transverse to the longitudinal axis of the stent, toward the second peak. The height of the second peak is sized so that as the stent is compressed to the first delivery diameter, the curved portion of the undulating link is longitudinally aligned with the second peak. To prevent contact among portions of the stent as the stent is crimped down prior to delivery into the body, the stent includes means for preventing contact between the undulating link and the second peak. This "means" can include an undulating link that has a J-shaped profile, or that has an angled portion on one side at the peak of the link, and/or other modifications further described in the Detailed Description and drawings, and their equivalents.

The stent design may also include structural features that improve such aspects as flexibility, the coatability of a drug coating onto the stent, flare reduction, and stent retention within the body.

Another embodiment prevents structural contact during crimping by utilizing an undulating link that has a special configuration. A flexible intravascular stent for use in a body lumen has cylindrical rings aligned along a common longitudinal axis and interconnected to form the stent. Each cylindrical ring has a first delivery diameter and a second implanted diameter. At least some of the cylindrical rings have first peaks and second peaks, with each of the peaks having a height, the second peaks being shorter than the first peaks. At least one undulating link attaches each cylindrical ring to an adjacent cylindrical ring. These undulating links have a curved portion extending transverse to the stent longitudinal axis toward the second peak. Each undulating link also has an arm having a first substantially straight portion that is substantially parallel to the longitudinal axis and a second, angled portion leading to the curve.

Another embodiment further improves retention of the stent within the body. In this embodiment, a flexible intravascular stent has a plurality of cylindrical rings aligned along a common longitudinal axis and interconnected to form the stent. Each cylindrical ring has a first delivery diameter and a second implanted diameter. At least some of the cylindrical rings have first peaks and second peaks, each of the peaks having a height, the second peaks being shorter than the first peaks. The stent also has an end ring having a plurality of first peaks and second peaks having a height, the height of the first and second peaks being uniform.

Another embodiment of the invention reduces the minimum diameter of the stent when it is crimped, prior to insertion into the body. In this embodiment, a flexible intravascular stent has a plurality of cylindrical rings aligned along a common longitudinal axis. At least one link connects adjacent cylindrical rings. The stent has a proximal end ring, which has five symmetric crests of equal height. The stent may optionally have different cell designs, with a first cell having two long crests and one short crest, and a second cell having one long crest and one short crest.

The above and other objects and advantages of this invention will be apparent from the following more detailed description when taken in conjunction with the accompanying drawings of exemplary embodiments.

BRIEF DESCRIPTION OF THE DRAWINGS

FIG. 1 is an elevational view, partially in section, of a prior art stent mounted on a rapid-exchange delivery catheter and positioned within an artery;

FIG. 2 is an elevational view, partially in section, similar to that shown in FIG. 1 wherein the prior art stent is expanded within the artery, so that the stent embeds within the arterial wall;

FIG. 3 is an elevational view, partially in section, showing the expanded prior art stent implanted within the artery after withdrawal of the rapid-exchange delivery catheter;

DETAILED DESCRIPTION OF THE PREFERRED EMBODIMENTS

Figure 4:
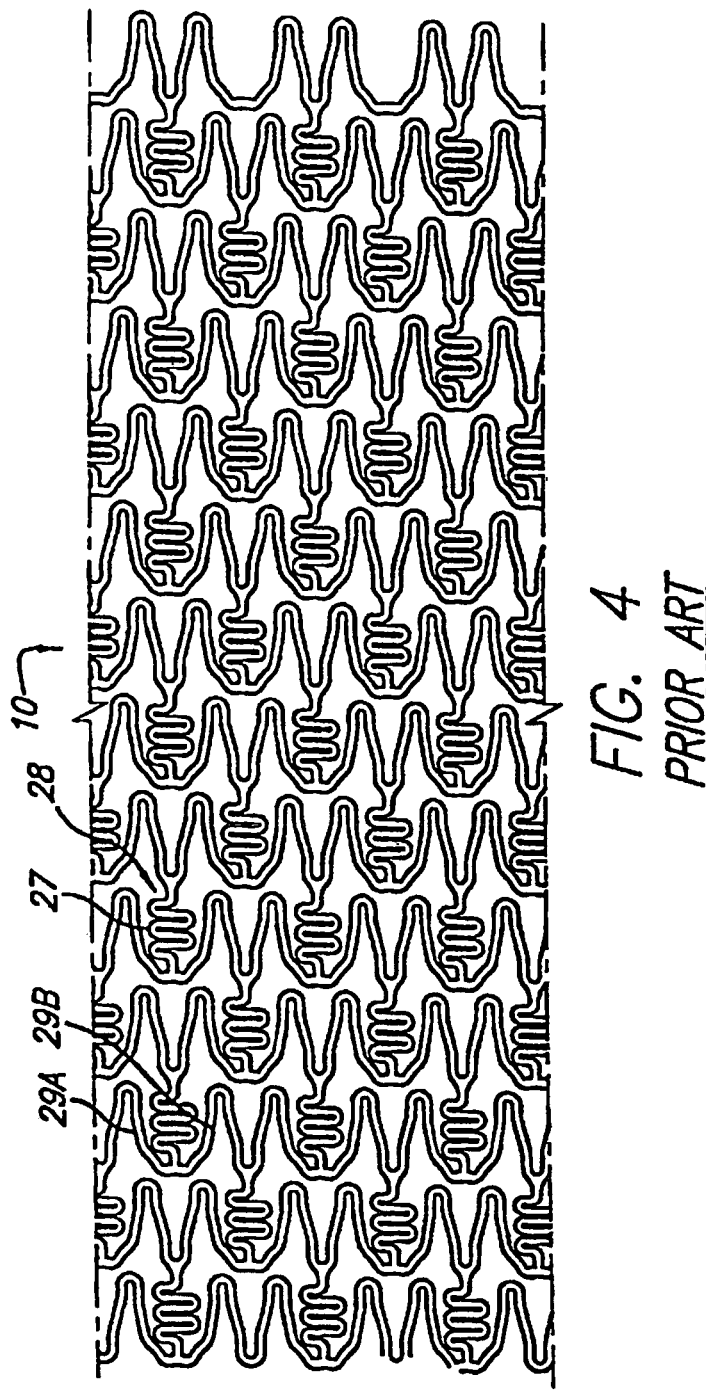
FIG. 4 is a plan view of a flattened prior art stent which illustrates the pattern of the stent shown in FIGS. 1-3.

Turning to the drawings, FIG. 1 depicts a prior art stent 10 mounted on a conventional catheter assembly 12. The assembly 12 is used to deliver and implant the stent in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system over a guide wire by any of the well known methods of an over the wire system (not shown) or by a well known rapid exchange catheter system, such as the one shown in FIG. 1.

Catheter assembly 12 as depicted in FIG. 1 is of the well known rapid exchange type which includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen that receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque that has been previously treated by an angioplasty or other repair procedure. Stent 10 is used to repair a diseased or damaged arterial wall which may include the plaque 26 as shown in FIG. 1, or a dissection, or a flap which are sometimes found in the coronary arteries, peripheral arteries and other vessels.

In a typical procedure to implant prior art stent 10, the guide wire 18 is advanced through the patient's vascular system by known methods so that the distal end of the guide wire is advanced past the plaque or diseased area 26. Prior to implanting the stent, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the prior art stent expanded and pressed against the vessel wall, and in FIG. 3, the implanted stent remains in the vessel after the balloon has been deflated and the catheter assembly and guide wire have been withdrawn from the patient.

The prior art stent 10 serves to hold open the artery after the catheter is withdrawn, as illustrated by FIG. 3. Due to the formation of the stent from an elongated tubular member, the undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with endothelial cell growth which further minimizes blood flow interference. The undulating portion of the stent provides good tacking characteristics to prevent stent movement within the artery. Furthermore, the closely spaced cylindrical elements at regular intervals provide uniform support for the wall of the artery, and consequently are well adapted to tack up and hold in place small flaps or dissections in the wall of the artery, as illustrated in FIGS. 2 and 3.

One of the problems associated with some prior art stents such as the one shown in FIG. 4, is the ability to more tightly crimp or compress the stent 10 onto the balloon portion of the catheter. For example, the undulating portion 27 of the links 28 of the prior art stent in FIG. 4 are positioned between two struts 29A/29B so that as the stent is tightly crimped or compressed onto the balloon portion of the catheter, the struts can only come so close to the undulating portion before contact is made.

Other Prior Art Designs

Figure 5A:
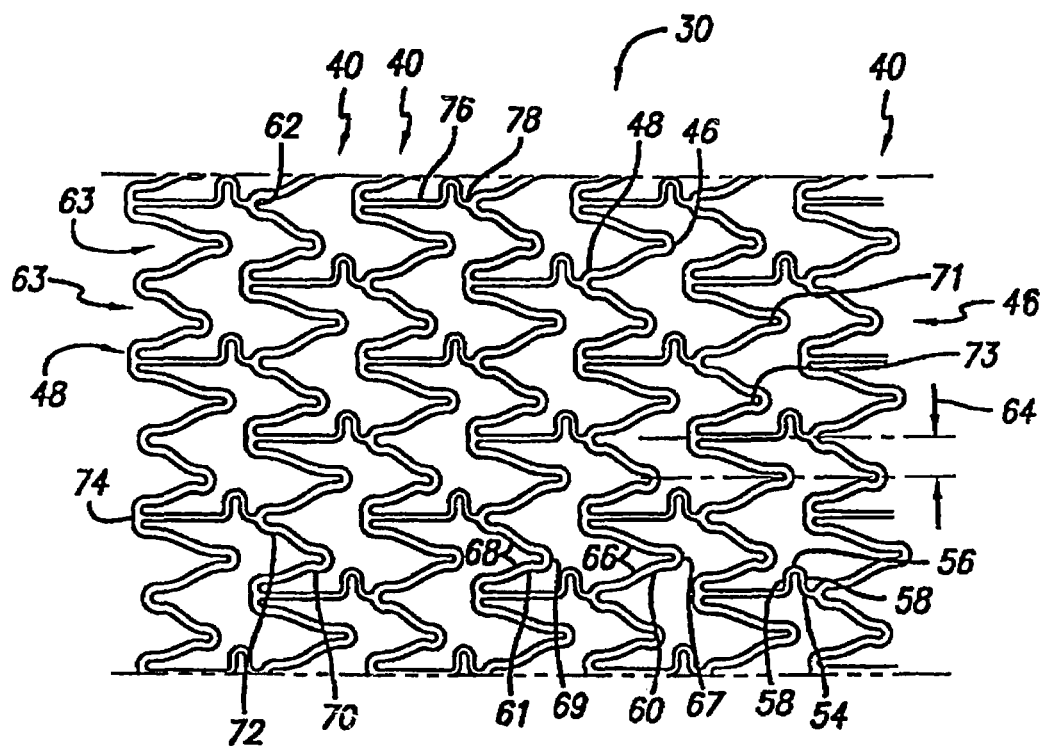
FIG. 5A is a plan view of a flattened stent of one embodiment of the invention which illustrates the pattern of the rings and links.
Figure 5B:
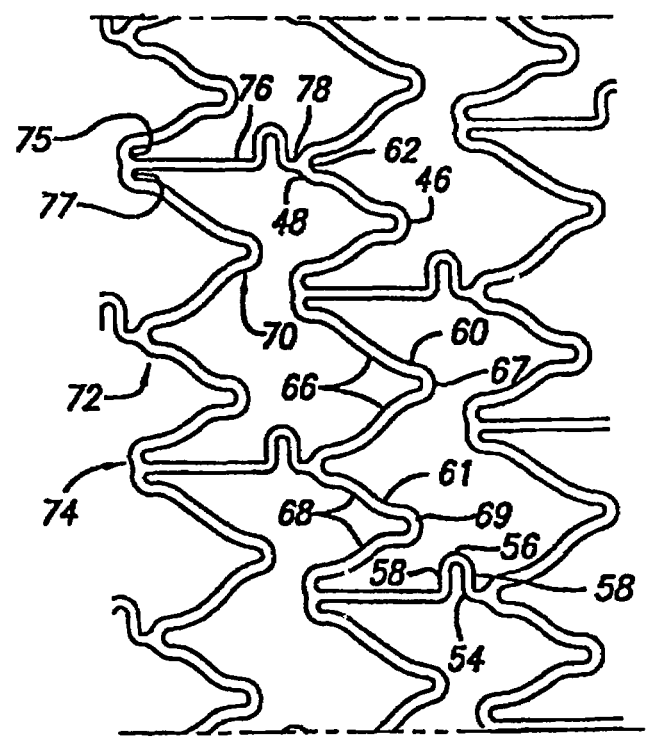
FIG. 5B is a partial plan view of the stent of FIG. 6A which has been expanded to approximately 3.0 mm inside diameter.
Figure 5C:
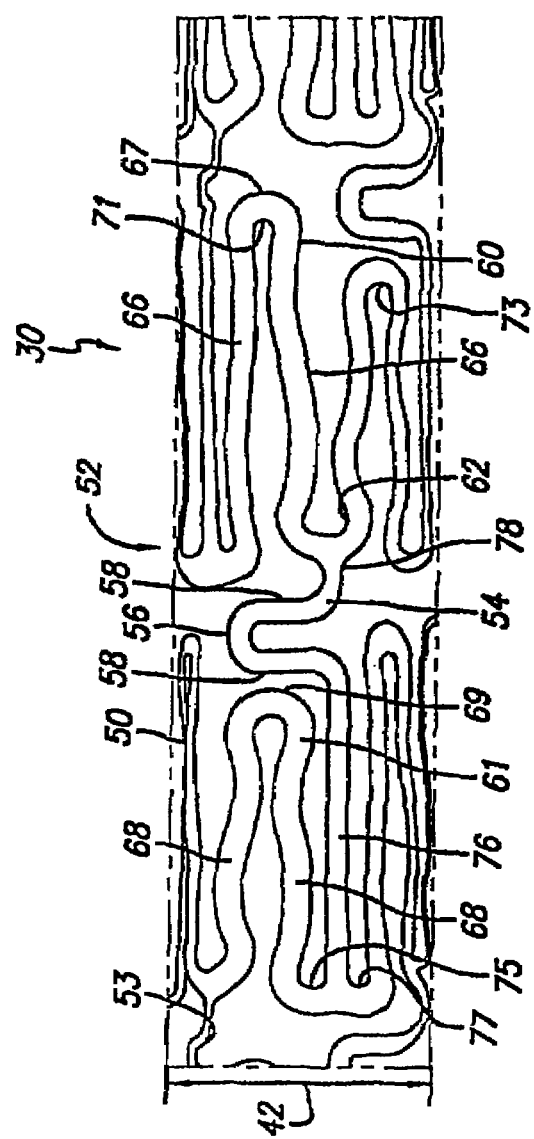
FIG. 5C is a plan view of a portion of the stent of FIG. 6A rolled into a cylindrical configuration and tightly crimped so that the various stent struts are either in close contact or contacting each other.

FIGS. 5A-5C depict a stent 30 in various configurations. Referring to FIG. 5A, for example, stent 30 is shown in a flattened condition so that the pattern can be clearly viewed, even though the stent is in a cylindrical form in use, such as shown in FIG. 5C. The stent is typically formed from a tubular member. However, it can be formed from a flat sheet such as shown in FIG. 5A and rolled into a cylindrical configuration as shown in FIG. 5C.

Each cylindrical ring 40 defines a cylindrical plane 50 (FIG. 5C) which is a plane defined by the proximal and distal ends 46, 48 of the ring and the circumferential extent as the cylindrical ring travels around the cylinder. Each cylindrical ring includes cylindrical outer wall surface 52 defining the outermost surface of the stent, and cylindrical inner wall surface 53 defining the innermost surface of the stent. Cylindrical plane 50 follows the cylindrical outer wall surface.

Undulating link 54 is positioned within cylindrical plane 50. The undulating links connect one cylindrical ring 30 to an adjacent cylindrical ring 30 and contribute to the overall longitudinal flexibility to the stent due to their unique construction. The flexibility of the undulating links derives in part from curved portion 56 connected to straight portions 58 wherein the straight portions are substantially perpendicular to the longitudinal axis of the stent. Thus, as the stent is being delivered through a tortuous vessel, such as a coronary artery, the curved portions 56 and straight portions 58 of the undulating links will permit the stent to flex in the longitudinal direction which substantially enhances delivery of the stent to the target site.

As shown in FIGS. 5A-5C, each of the cylindrical rings has a plurality of first peaks 60 which have first struts 66 attached to a first apex 67. The cylindrical rings also have second peaks 61 which have second struts 68 attached to a second apex 69. The length of the second struts 68 is typically shorter than the length of the first struts 66. As can be seen in FIGS. 5C, when the stent is in a crimped condition, or a partially crimped condition, the first struts and second struts respectively will be closer to each other when the stent is compressed or crimped onto the balloon or expandable member of the catheter.

Referring to FIGS. 5A-5C, the stent 30 can be described as having cylindrical rings formed of U-shaped portions 70, portions 72, and W-shaped portions 74. Again, while the stent is generally laser cut from a tube and it typically has no discreet parts, for ease of identification the stent of the invention also can be referred to as having U- and W-shaped portions, as appropriate for the embodiment. The U-shaped portions have no supporting structure attached thereto. The W portion has at its base or curve portion an arm 78 which attaches at the other end of the undulating link. The length of the arms attaching the links to the rings and shape can vary.

The stent 30 can be mounted on a balloon catheter similar to that shown in the prior art device in FIG. 1. The stent is tightly compressed or crimped onto the balloon portion of the catheter and remains tightly crimped onto the balloon during delivery through the patient's vascular system. When the balloon is expanded, the stent expands radially outwardly into contact with the body lumen, for example, a coronary artery. When the balloon portion of the catheter is deflated, the catheter system is withdrawn from the patient and the stent remains implanted in the artery. Similarly, if the stent of the present invention is made from a self-expanding metal alloy, such as nickel-titanium or the like, the stent may be compressed or crimped onto a catheter and a sheath (not shown) is placed over the stent to hold it in place until the stent is ready to be implanted in the patient. Such sheaths are well known in the art. Further, such a self-expanding stent may be compressed or crimped to a delivery diameter and placed within a catheter. Once the stent has been positioned within the artery, it is pushed out of the catheter or the catheter is withdrawn proximally and the stent held in place until it exits the catheter and self-expands into contact with the wall of the artery. Balloon catheters and catheters for delivering self-expanding stents are well known in the art.

Coating the Stent with Drugs

Stents can also be coated with a drug or therapeutic agent to assist in repair of the bifurcated vessel and may be useful, for example, in reducing the likelihood of the development of restenosis. Further, it is well known that the stent (usually made from a metal) may require a primer material coating to provide a substrate on which a drug or therapeutic agent is coated, since some drugs and therapeutic agents do not readily adhere to a metallic surface. The drug or therapeutic agent can be combined with a coating or other medium used for controlled release rates of the drug or therapeutic agent. Examples of therapeutic agents that are available as stent coatings include rapamycin, everolimus, actinomycin D (ActD), or derivatives and analogs thereof. ActD is manufactured by Sigma Aldrich, 1001 West Saint Paul Avenue, Milwaukee, Wis. 53233, or COSMEGEN, available from Merck. Synonyms of actinopmycin D include dactinomycin, actinomycin IV, actinomycin 11, actinomycin X1, and actinomycin C1. Examples of agents include other antiproliferative substances as well as antineoplastic, antinflammatory, antiplatelet, anticoagulant, antifibrin, antithomobin, antimitotic, antibiotic, and antioxidant substances. Examples of antineoplastics include taxol (paclitaxel and docetaxel). Examples of antiplatelets, anticoagulants, antifibrins, and antithrombins include sodium heparin, low molecular weight heparin, hirudin, argatroban, forskolin, vapiprost, prostacyclin and prostacyclin analogs, dextran, D phe pro arg chloromethylketone (synthetic antithrombin), dipyridamole, glycoprotein, 11b/111a platelet membrane receptor antagonist, recombinant hirudin, thrombin inhibitor (available from Biogen), and 7E 3B® (an antiplatelet drug from Centocore). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen), angiotensin converting enzyme inhibitors such as Captopril (available from Squibb), Cilazapril (available from Hoffman LaRoche), or Lisinopril (available from Merck);

calcium channel blockers (such as Nifedipine), colchicine fibroblast growth factor (FGF) antagonists, fish oil (omega 3 fatty acid), histamine antagonist, Lovastatin (an inhibitor of HMG-CoA reductase, a cholesterol lowering drug from Merck), monoclonal antibodies (such as PDGF receptors), nitroprusside, phosphodiesterase inhibitors, prostaglandin inhibitor (available from Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone.

It should be understood that any reference in the specification or claims to a drug or therapeutic agent being coated on the stent is meant that one or more layers can be coated either directly on the stent or onto a primer material on the stent to which the drug or therapeutic agent readily attaches.

Stent Design for Reducing Contact and Protecting the Drug Coating

Figure 6:
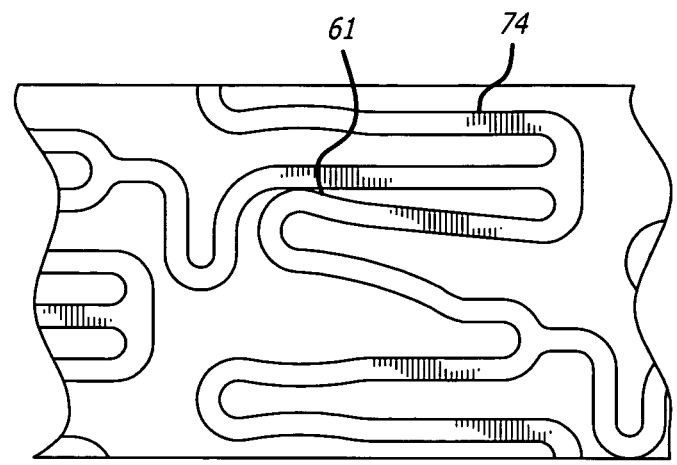
FIG. 6 is a plan view of a prior art stent in a crimped or compressed configuration depicting metal-to-metal contact between two portions of the stent, thereby causing damage to the drug coating that is on the stent.

Considering particular problems that may arise with some prior art stents, FIG. 6 illustrates a stent that has been crimped prior to delivery within the body. The short crest 61 is seen in FIG. 6 to be in contact with a middle connector of the crest 74. In particular, a portion of the short crest 61 is in interference with a metal member 74, such that any drug coating that is on the respective points of contact may be damaged.

Figure 7:
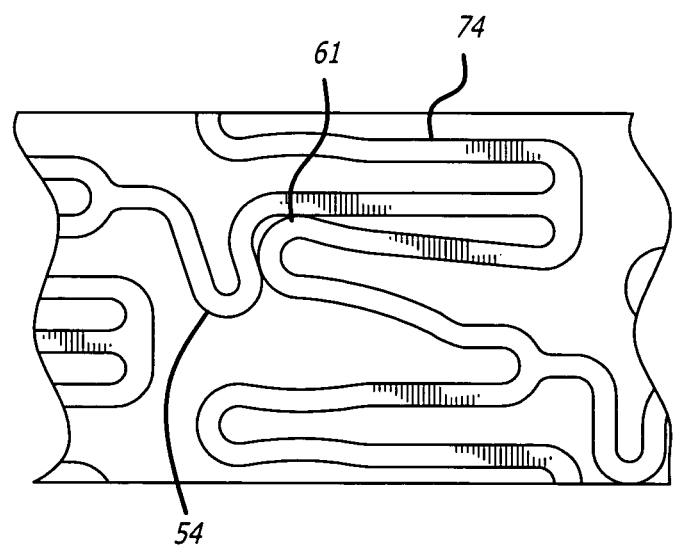
FIG. 7 is a plan view of a prior art stent in a crimped or compressed configuration depicting even greater metal-to-metal contact between two portions of the stent than in FIG. 19.

An even more serious situation is illustrated in FIG. 7. In this scenario, the non-linear link 54 is also in contact with the short crest 61. In this case, the short crest 61 is nested in between the non-linear link 54 and the respective middle connector of the crest 74. Consequently, there are two points of metal-to-metal contact. In the scenario of FIG. 7, even more of the drug coating on the stent is damaged in this crimped configuration.

At this juncture, it is noted that the term "metal-to-metal contact" is a term of convenience. The phrase refers to two portions of the stent coming into contact when the stent is crimped. However, "metal-to-metal contact" as used herein may also apply to stents that are made of materials other than metal, such as stents that are made from a polymer or materials to be developed in the future.

It is a considerable challenge to design a stent pattern that will avoid metal-to-metal contact. By creating such a design, the problems that arise with damage to the drug coating from metal-to-metal contact can be eliminated. Consequently, the drug coating may maintain its integrity, and function as a drug eluting coating for the desired period of time.

Figure 8:
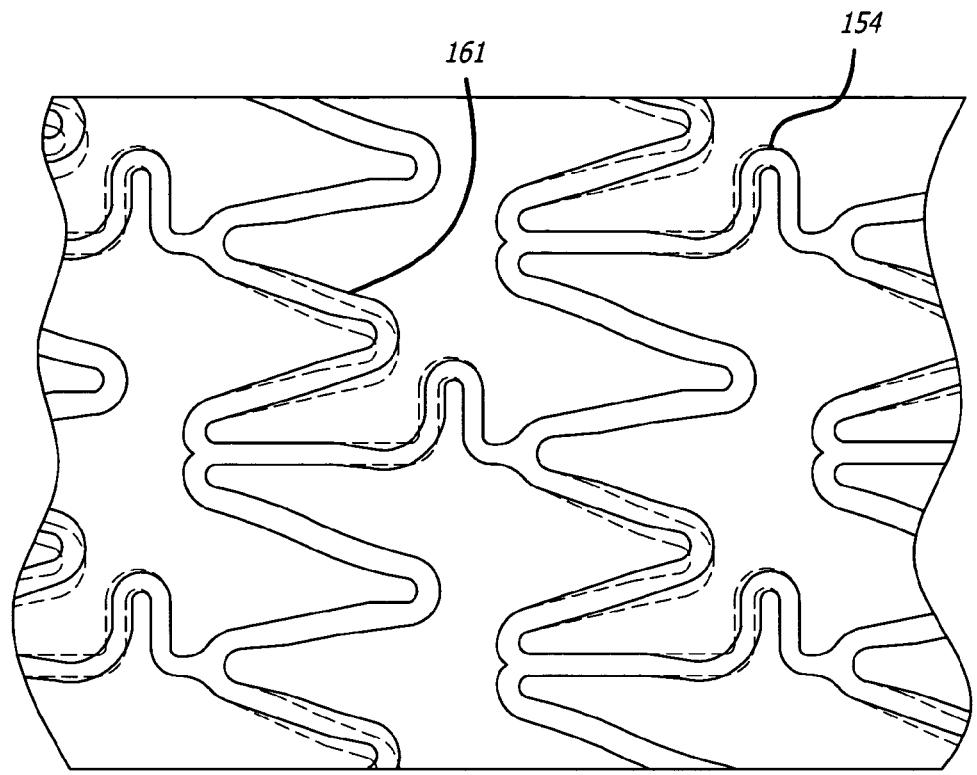
FIG. 8 illustrates one embodiment of the present invention.
Figure 9:
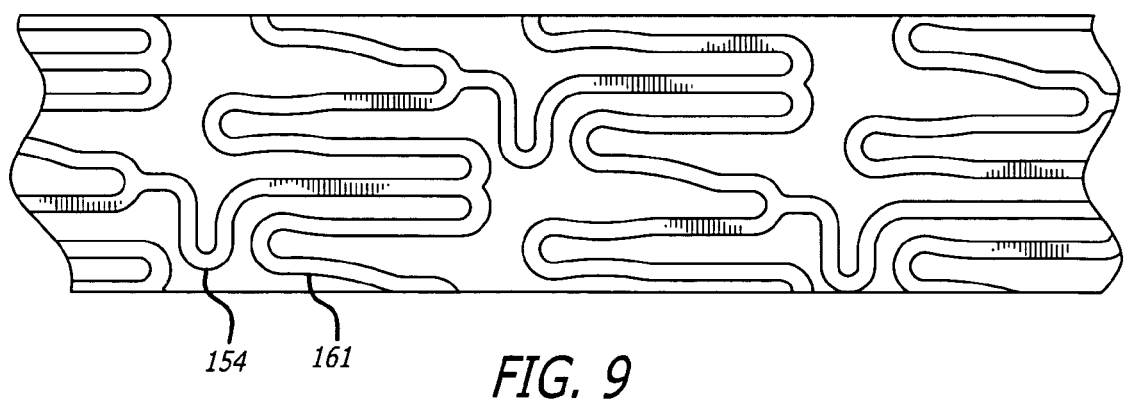
FIG. 9 depicts a design that eliminates metal-to-metal contact, allowing the stent to be crimped without damage to the drug coating.

Considering now an embodiment of the present invention, for example, FIG. 8 illustrates a stent pattern in which the short crest 161 is modified. In particular, the prior design is shown in dotted lines, whereas the new design that has been modified is shown in solid lines. With the modified short crest 161, the upward angulation is changed such that the short crest is lifted upward compared to the original short crest design. At the same time, the non-linear link 154 is modified to have more of a "J" shaped configuration. This combination of a short crest having a modified upward angulation with a modified, "J" shaped non-linear link 154 results in a stent design that can be crimped without suffering the metal-to-metal contact illustrated in FIGS. 6 and 7. Indeed, FIG. 9 illustrates the stent pattern of FIG. 8 when the corresponding stent is in a crimped configuration. In this configuration, the short crest 161 does not come into contact with a corresponding portion of the W crest, or with the corresponding linear link 154. The integrity of the drug coating is therefore maintained, such that the drug coating is not damaged during crimping.

Figure 10:
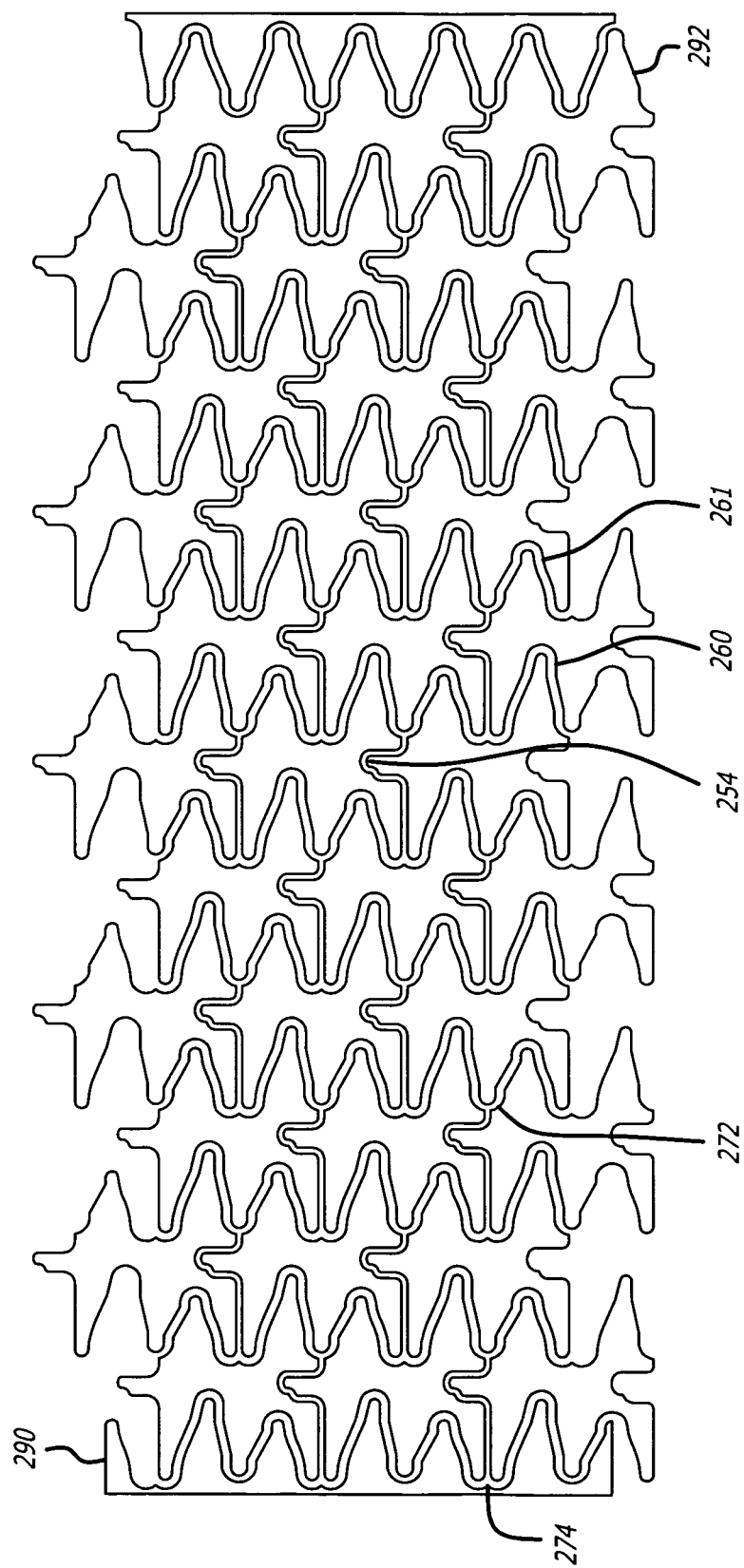
FIG. 10 is a plan view of a flattened stent of another embodiment of the invention which illustrates a pattern of the rings and links.

Turning to a second modified design, FIG. 10 illustrates another alternative stent pattern designed to reduce metal-to-metal contact. The design of FIG. 10 also results in increased flexibility, improved coatability, and better stent retention within the body as compared to the design in FIG. 5A. Specific features that have been modified in the design of FIG. 10, which will be discussed in greater detail below, include a modified non-linear link 254, a modified long crest 260, a modified short crest 261, a modified crest 272, and a modified W crest 274. Also, in one of the embodiments, the proximal end ring 292 is changed such that all of the crests, including both the short crests and the long crests, are of uniform length. The modification to the proximal end ring 292 can be seen when compared with the distal end ring 290, in which the short and long crests, 261 and 260, have different lengths.

Figure 11:
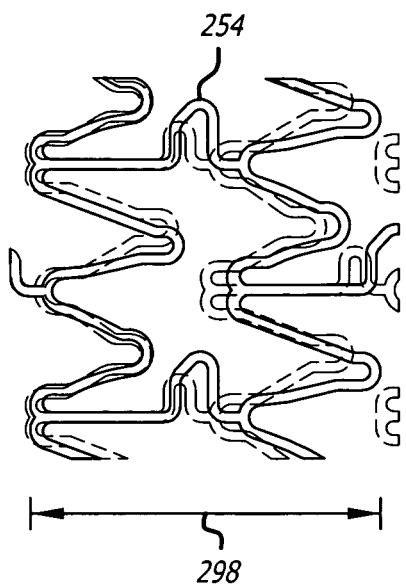
FIG. 11 is an enlarged partial plan view showing modifications to the cell length and bar arm portions of the stent of FIG. 10.

FIG. 11 illustrates two modified aspects of the stent design, as illustrated in FIG. 10. The first aspect relates to the cell length, which is a measure of the distance between rings. For example, the distance 298 in the design of FIG. 11 is greater than the corresponding cell length in the design of FIG. 5A. This longer cell length has been determined to improve the flexibility of the stent within the body. At the same time, the bar arms in FIG. 11 are seen to be less filleted as compared to the corresponding bar arms in the design of FIG. 5A. These less filleted bar arms help to reduce metal-to-metal contact during crimping. Again, it is noted in FIGS. 11-18 that the new design is shown in solid black line, whereas the old design is shown in broken line.

Figure 12:
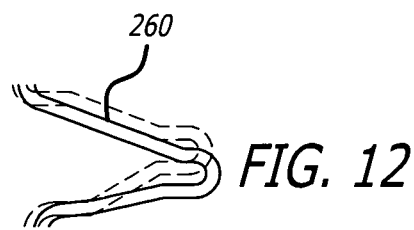
FIG. 12 is an enlarged partial plan view showing modifications to the long crest portions of the stent of FIG. 10.

Considering FIG. 12, the long crest 260 is shown now to be angled away from the non-linear link. In one embodiment, the long crest is angled away from the non-linear link by approximately 6.5 degrees. Of course, other angles may be used as desired. This angling away from the non-linear link also contributes to reducing metal-to-metal contact when the stent is crimped.

Figure 13:
FIG. 13 is an enlarged partial plan view showing modifications to the non-linear link portions of the stent of FIG. 10.

FIG. 13 illustrates a non-linear link that is taller and wider than its corresponding non-linear link in the design of FIG. 5A. This taller and wider non-linear link 254 helps to improve the flexibility of the modified stent. The non-linear link 254 is also shown to be angled. This angling helps to reduce metal-to-metal contact when the stent is crimped.

Figure 14:
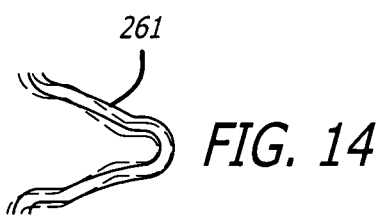
FIG. 14 is an enlarged partial plan view showing modifications to the short crest portions of the stent of FIG. 10.

FIG. 14 illustrates a modification that may be made to the short crest 261. The short crest is slightly shorter than the corresponding short crest of FIG. 5A. Also, the short crest radii is somewhat increased as compared to the original design. The increased radii of the short crest 261 may help to improve coatability of the stent. That is, the greater radii helps reduce what is known in the art as "webbing." Webbing is a well known problem in which the drug coating in certain regions of the stent becomes non-uniform. Consequently, by increasing the radius, the likelihood of webbing is decreased.

Figure 15:
FIG. 15 is an enlarged partial plan view showing modifications made to the Y crest portions of the stent of FIG. 10.

Turning to the crest 272 of FIG. 15, the crest radius is increased somewhat as compared to the original design of FIG. 5A. Again, this larger radius helps improve the coatability of the stent. The drug coating on the larger radius is less likely to web, thereby helping to foster more uniform distribution of the drug after deployment within the body.

Figure 16:
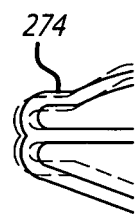
FIG. 16 is a an enlarged partial plan view showing modifications made to the W crest portions of the stent of FIG. 10.

FIG. 16 illustrates a modification to the W crest 274. The W configuration is more "open" than in the previous designs. This more open W crest 274 also helps to reduce the likelihood of webbing, and improve the coatability of the stent.

Figure 17:
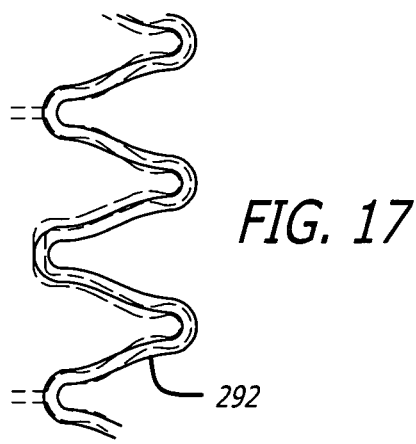
FIG. 17 is an enlarged partial plan view showing modifications made to the proximal end ring of the stent of FIG. 10.

FIG. 17 illustrates a proximal end ring 292. As can be seen by comparing the solid lines with the broken lines of the previous configuration, the modified proximal end ring is somewhat wider than the original design. This additional width helps to foster better stent retention once the stent is deployed. It is also noted that no W crest is used in this proximal end ring. The pattern of all crests in the proximal end ring having a uniform length, helps to improve stent retention within the vessel.

Figure 18:
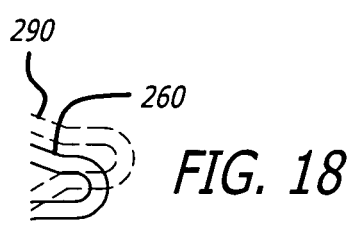
FIG. 18 is an enlarged partial plan view showing modifications made to the distal end ring of the stent of FIG. 10.

FIG. 18 illustrates a portion of the distal end ring 290, in which the distal end ring 290 is somewhat wider than the corresponding distal end ring in the design of FIG. 5A. Also, the long crest 260 is wider in the crest region on the distal end ring 290 of the modified design, than in the original.

The foregoing combination of features leads to a stent design having a number of improved properties. One such property is increased flexibility, while others include improved coatability and reduced likelihood of webbing. A further improved property is better stent retention, as a result of modifications to the proximal end ring 292. Most importantly, the modified stent design of FIG. 10 reduces the likelihood of metal-to-metal contact, thereby protecting the integrity of the drug coating on the stent and improving drug delivery within the body.

Figure 19:
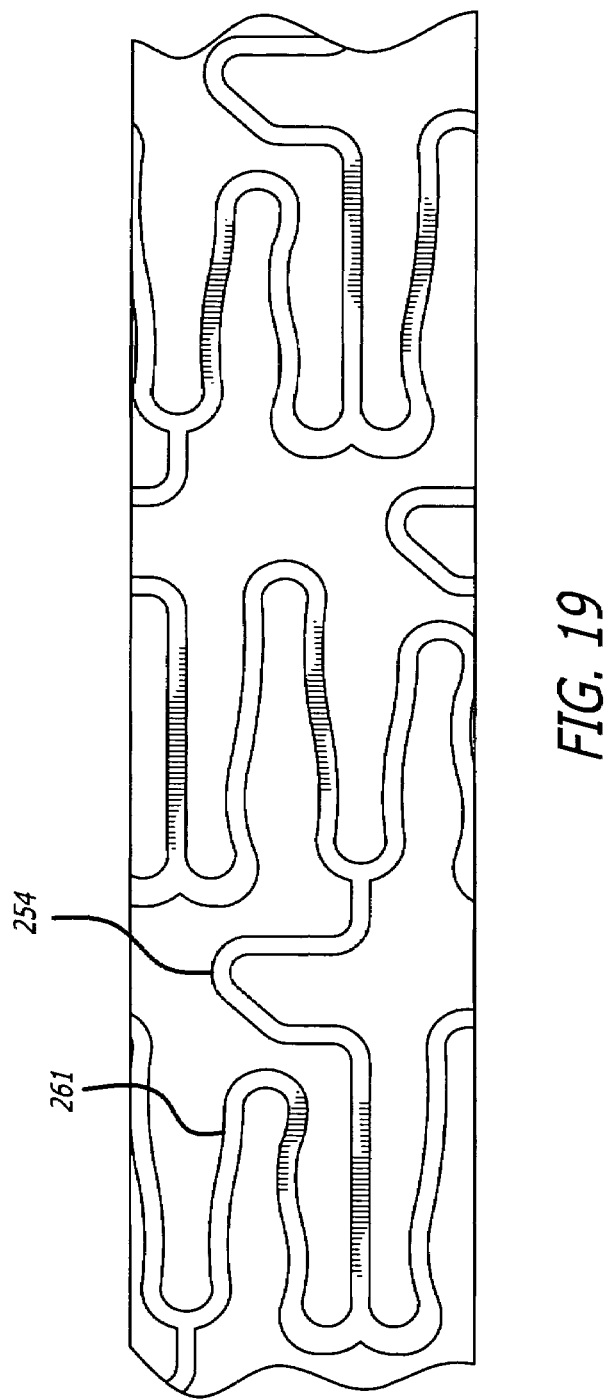
FIG. 19 is an enlarged partial plan view illustrating how metal-to-metal contact is prevented as a result of the stent design.

FIG. 19 illustrates the stent of FIG. 10 as it appears in the crimped configuration. As can be seen in FIG. 19, there is no metal-to-metal contact and consequently no damage to the drug coating when the stent is crimped. As can be seen in FIG. 19, the non-linear link 252, having the angled upper portion, stays comfortably away from the corresponding tip of the adjacent short crest.

In summary, the modifications illustrated in FIGS. 10-19 can be categorized as follows. The following features help to improve flexibility of the stent: longer cell length, and taller and wider non-linear links. The following features can be said to reduce metal-to-metal contact: the long crest being angled away from the non-linear link, the angled non-linear link having two different bends as opposed to a rounded non-linear link with symmetric bends, and less filleted bar arms. The following features help to improve coatability and reduce the likelihood of webbing: a larger short crest radii, a larger crest radii, more open W crest radii. Additional effects of modifications made in FIGS. 10-19 include less likelihood of flaring with the uniform proximal end ring 292 in which there is no W crest in the proximal end ring. Also, the wider proximal and distal end rings help to improve stent retention.

It is noted that in the context of this patent application. There are various "means" for accomplishing important design functions of the stent. The following is a non-limiting recital of different "means" disclosed herein. It should be understood that this list is non-limiting, and that particular "means" may include additional features and/or combinations of features other than those listed below. "Means for improving flexibility" refers to a longer cell length, and/or taller and wider non-linear link. "Means for reducing contact" refers to the long crest being angled away from the non-linear link, the angled non-linear link with two different bends as opposed to a rounded non-linear link with symmetric bends, for example, a non-linear link having a "J" shape profile, and/or less filleted bar arms as compared to the design of FIG. 5A. "Means for improving coatability" refers to the larger short crest radius, the larger crest radius, and a more open W crest radius. "Means for reducing flaring" refers to an end ring design in which all of the crests are uniform in length and in which there is no W crest in the end ring. Finally, "means for improving stent retention" refers to wider proximal and/or wider distal end rings.

Stent Having a Proximal End Ring with Five Symmetric Crests

A further improvement to stent design may be made in order to reduce the diameter of the stent when it is crimped. In this approach, one crest from the proximal end ring is removed so that there is less material to crimp down. In particular, the stent design of Fig. 20 has five symmetric crests on the end ring 392 instead of six crests. Also, there are only two non linear links 354, 355 in the proximal end ring of this design.

The distal end ring 390, by contrast, has a "W" crest 374, and corresponding long and short crests. In one alternative embodiment, the distal end ring 390 may have the same structure as the proximal end ring 392, although the embodiment of FIG. 20 as illustrated has different structures for the distal and proximal end rings.

Figure 20:
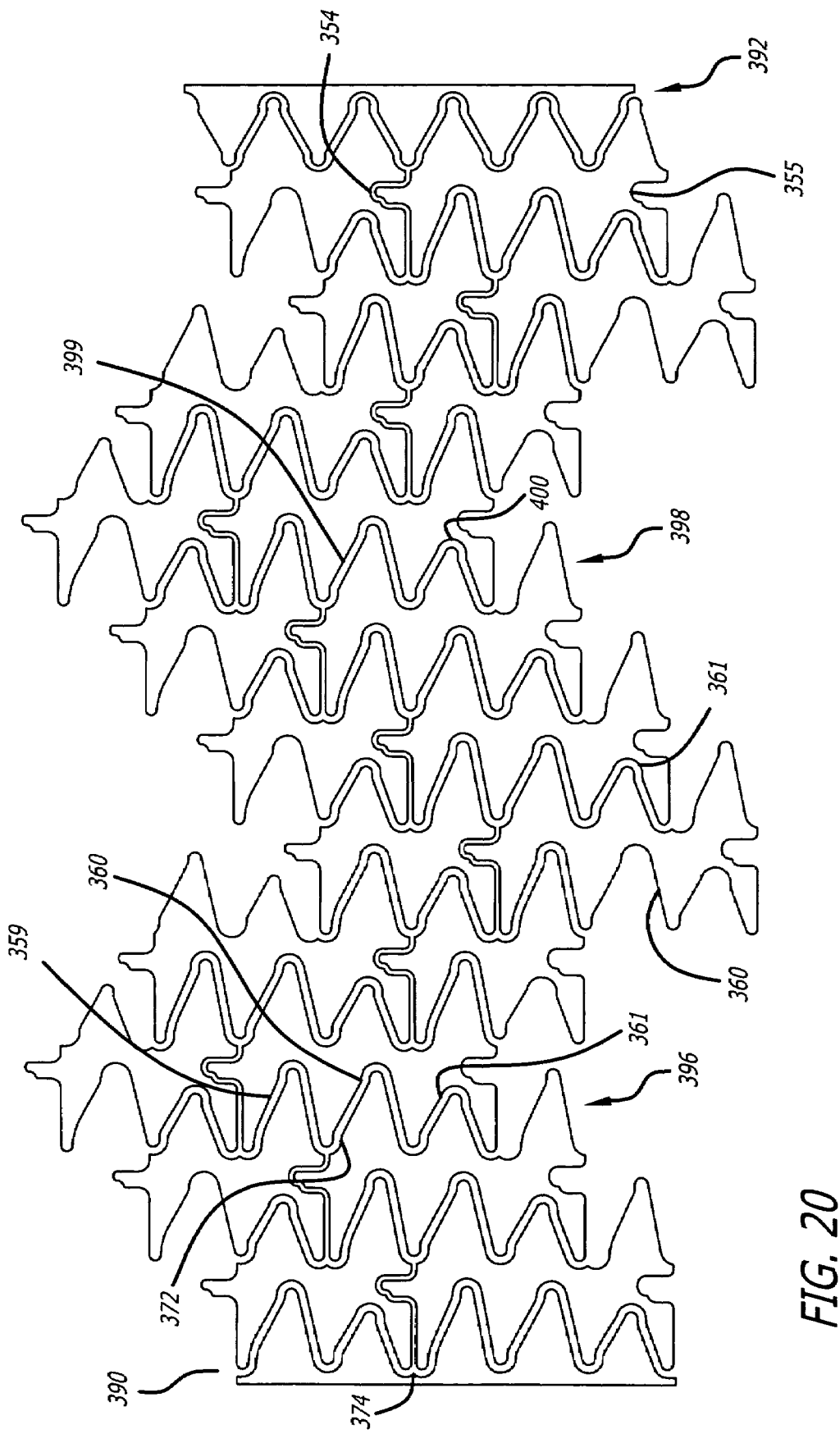
FIG. 20 is a plan view of a flattened stent of another embodiment of the invention which illustrates a pattern of the rings and links.

A further improvement relates to the cell structure of the stent of FIG. 20. In one cell 396, there are two long crests 359, 360 and one short crest 361. In the second cell, there is one long crest 399 and one short crest 400. This is in contrast to the design of FIG. 5A, for example, in which there is one long crest and one short crest per cell. The non linear link in the design of FIG. 20 (e.g. 354) is also somewhat smaller, to allow more room for crimping to a smaller diameter.

In light of the foregoing, "means for reducing minimum crimp diameter" refers to the five symmetric crest design and structural equivalents thereof.

Methods of Stent Manufacture

A stent according to the present invention can be made in many ways known in the art. As non-limiting examples, methods of manufacturing stents are described in U.S. patent application Ser. No. 10/946,223, entitled, "Pulsed Fiber Laser Cutting System For Medical Implants," published as Publication No. US 2005/0035101, and in U.S. patent application Ser. No. 11/278,131, entitled, "Pulsed Synchronized Laser Cutting Of Stents" filed on Mar. 30, 2006, both of which are incorporated by reference herein. Similarly, U.S. Pat. No. 6,521,865, issued on Feb. 18, 2003 and entitled,"Pulsed Fiber Laser Cutting System for Medical Implants," is also incorporated by reference herein.

Materials from Which a Stent May be Made

The stent of the present invention can be made from any of a wide variety of stent materials known in the art. As non-limiting examples, such materials may include stainless steel, cobalt, chromium, tantalum, titanium, nickel-titanium, nickel-titanium-vanadium, Elgiloy®, and various polymers. While stainless steel is often used, many other materials, such as shape memory alloys or polymers may be used. Shape memory alloys are well known and include, but are not limited to, nickel-titanium and nickel-titanium-vanadium. Any of the shape memory alloys can be formed into a tube and laser cut in order to form the pattern of the stent of the present invention. As is well known, the shape memory alloys of the stent of the present invention can include the type having superelastic or thermoelastic martensitic transformation, or display stress-induced martensite.

Importantly, a stent formed of shape memory alloys, whether the thermoelastic or the stress-induced martensite-type, can be delivered using a balloon catheter of the type described herein, or be delivered via a catheter without a balloon or a sheath catheter.

Conclusion

While the invention has been illustrated and described herein, in terms of its use as an intravascular stent, it will be apparent to those skilled in the art that the stent can be used in other body lumens. Further, particular sizes and dimensions, number of undulations or U-shaped portions per ring, materials used, and the like have been described herein and are provided as examples only. It is further noted that while many different structural aspects have been discussed herein, the invention relates both to structural aspects as considered alone, as well as two or more aspects in combination. That is, it is to be emphasized that the invention resides in various combinations of elements, as outlined in the claims. Other modifications and improvements may be made without departing from the scope of the invention.

We claim:

1. A flexible intravascular stent for use in a body lumen, comprising:
a plurality of cylindrical rings aligned along a common longitudinal axis and interconnected to form the stent, each cylindrical ring having a first delivery diameter and a second implanted diameter;
at least some of the cylindrical rings each having a plurality of first peaks and second peaks, each of the peaks having a height, the second peaks being shorter than the first peaks;
at least one undulating link attaching each cylindrical ring to an adjacent cylindrical ring, the undulating links having a width and a curved portion extending transverse to the stent longitudinal axis toward the second peak, the entire width of the curved portion having curvature along the length defining the curved portion;
the first peaks and the second peaks extending axially in the same direction and not being connected to an undulating link; and
at least one undulating link including a first arm which is substantially perpendicular to a longitudinal axis of the stent, the first arm being substantially straight and being connected to the curved portion, the at least one undulating link including a second arm having a first substantially straight portion which is substantially perpendicular to a longitudinal axis of the stent and a [second,] angled portion, the angled portion extending from the curved portion, wherein the angled portion of the second arm is adjacent to the second peak in the first delivery position and the entire width of the angled portion is substantially straight along the length defining the angled portion.

2. The stent of claim 1, wherein the stent is formed from a shape memory alloy.

3. The stent of claim 1, wherein the stent is formed from a superelastic or pseudoelastic metal alloy.

4. The stent of claim 1, wherein at least a portion of the stent has a variable thickness configuration.

5. The stent of claim 1, wherein at least some of the first peaks have a first radius and the second peaks have a second radius, the second radius being greater than the first radius.

6. The stent of claim 1, wherein at least some of the first peaks have a pair of first struts and at least some of the second peaks have a pair of second struts, the first struts being longer than the second struts.

7. The stent of claim 1, wherein the angled portion of the undulating link provides flexibility to the stent.

8. The stent of claim 1, wherein the angled portion reduces the likelihood of metal-to-metal contact when the stent is in a crimped configuration.

9. The stent of claim 1, wherein the stent further comprises a proximal ring having no W-shaped element which reduces the likelihood of flaring.

10. The stent of claim 1, wherein the stent further comprises a proximal end ring having a large radius of curvature in the peaks thereby improving stent retention.

11. A flexible intravascular stent for use in a body lumen, comprising:
a plurality of cylindrical rings aligned along a common longitudinal axis and interconnected to form the stent, each cylindrical ring having a first delivery diameter and a second implanted diameter;
at least some of the cylindrical rings each having a plurality of first peaks and second peaks, each of the peaks having a height, the second peaks being shorter than the first peaks;
at least one undulating link attaching each cylindrical ring to an adjacent cylindrical ring, each of the undulating links having a width and a curved portion extending transverse to the stent longitudinal axis toward the second peak, the height of the second peak being sized so that as the stent is compressed to the first delivery diameter, the curved portion of the undulating link is longitudinally aligned with the second peak and the entire width of the curved portion has curvature along the length defining the curved portion;
the first peaks and the second peaks extending axially in the same direction and not being connected to an undulating link; and
an angled portion extending from the curved portion and adjacent to the second peak, the angled portion thereby preventing contact between the at least one undulating link and the second peak when the stent is compressed to the first delivery diameter, the entire width of the angled portion being substantially straight along the length defining the angled portion.

12. The stent of claim 11, wherein at least one undulating link comprises at least one curved portion connected to a substantially straight portion, the substantially straight portion being substantially perpendicular to the stent longitudinal axis.

13. The stent of claim 12, wherein the substantially straight portion of the at least one undulating link is perpendicular to the stent longitudinal axis when the stent is in the first delivery diameter configuration.

14. The stent of claim 12, wherein the substantially straight portion of the at least one undulating link is perpendicular to the stent longitudinal axis when the stent is in the second implanted diameter configuration.

15. The stent of claim 11, wherein at least one of the undulating links comprise a plurality of curved portions.

16. The stent of claim 11, wherein the first peaks of each cylindrical ring are in phase with the first peaks of an adjacent cylindrical ring.

17. The stent of claim 11, wherein the stent is formed from a shape memory alloy.

18. The stent of claim 11, wherein the stent is formed from a superelastic or pseudoelastic metal alloy.

19. The stent of claim 11, wherein at least a portion of the stent has a variable thickness configuration.

20. The stent of claim 11, wherein the first peaks have a first radius and the second peaks have a second radius, the second radius being greater than the first radius.

21. The stent of claim 11, wherein each of the first peaks has a pair of first struts and each of the second peaks has a pair of second struts, the first struts being longer than the second struts.

22. The stent of claim 11, wherein the stent comprises an end ring having a plurality of first peaks and second peaks having a height, the height of the first and second peaks being uniform.

23. The stent of claim 11, wherein the angled portion of the undulating link provides flexibility to the stent.

24. The stent of claim 11, wherein the angled portion reduces the likelihood of metal-to-metal contact when the stent is in a crimped configuration.

25. The stent of claim 11, wherein the stent further a proximal end ring having no W-shaped element which reduces the likelihood of flaring.

26. The stent of claim 11, wherein the stent further comprises a proximal end ring having a large radius of curvature in the peaks thereby improving stent retention.

27. A flexible intravascular stent for use in a body lumen, comprising:
- a plurality of cylindrical rings aligned along a common longitudinal axis and interconnected to form the stent, each cylindrical ring having a first delivery diameter and a second implanted diameter;
- at least some of the cylindrical rings each having a plurality of first peaks and second peaks, each of the peaks having a height, the second peaks being shorter than the first peaks;
- at least one undulating link attaching each cylindrical ring to an adjacent cylindrical ring, each of the undulating links having a width and a curved portion extending transverse to the stent longitudinal axis toward the second peak, the entire width of the curved portion having curvature along the length defining the curved portion;
- an angled portion extending from the curved portion and positioned adjacent the second peak in order to reduce the likelihood of metal-to-metal contact when the stent is in the delivery diameter configuration and the entire width of the angled portion is substantially straight along the length defining the angled portion;
- the first peaks and the second peaks extending axially in the same direction and not being connected to an undulating link; and
- an end ring having a plurality of first peaks and second peaks having a height, the height of the first and second peaks being uniform.

28. The stent of claim 27, wherein at least one undulating link comprises at least one curved portion connected to a substantially straight portion, the substantially straight portion being substantially perpendicular to the stent longitudinal axis.

29. The stent of claim 28, wherein the substantially straight portion of the at least one undulating link is perpendicular to the stent longitudinal axis when the stent is in the first delivery diameter configuration.

30. The stent of claim 27, wherein at least one of the undulating links comprise a plurality of curved portions.

31. The stent of claim 27, wherein the first peaks of each cylindrical ring are in phase with the first peaks of an adjacent cylindrical ring.

32. The stent of claim 27, wherein the stent is formed from any of the group of metal alloys consisting of stainless steel, tantalum, nickel-titanium, cobalt-chromium and titanium.

33. The stent of claim 27, wherein the stent is formed from a shape memory alloy.

34. The stent of claim 27, wherein the stent is formed from a superelastic or pseudoelastic metal alloy.

35. The stent of claim 27, wherein at least a portion of the stent has a variable thickness configuration.

36. The stent of claim 27, wherein the first peaks have a first radius and the second peaks have a second radius, the second radius being greater than the first radius.

37. The stent of claim 27, wherein each of the first peaks has a pair of first struts and each of the second peaks has a pair of second struts, the first struts being longer than the second struts.

38. The stent of claim 27, in which the angled portion of the undulating link provides flexibility to the stent.

39. The stent of claim 27, in which the angled portion reduces the likelihood of metal-to-metal contact when the stent is in a crimped configuration.

40. The stent of claim 27, in which the stent further a proximal ring having no W-shaped element which reduces the likelihood of flaring.

41. The stent of claim 27, in which the stent further comprises a proximal end ring having a large radius of curvature in the peaks thereby improving stent retention.

42. The stent of claim 1, wherein the first arm is longer than the first substantially straight portion of the second arm.

* * * * *